(12) United States Patent
Schook et al.

(10) Patent No.: US 9,314,020 B2
(45) Date of Patent: Apr. 19, 2016

(54) MICROBICIDAL COMPOSITION

(71) Applicant: Dow Global Technologies LLC, Midland, MI (US)

(72) Inventors: Paul O. Schook, Lake Zurich, IL (US); Freddie L. Singleton, Vernon Hills, IL (US); Sheila M. Tinetti, Vernon Hills, IL (US); Bei Yin, Phoenixville, PA (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 14/427,001

(22) PCT Filed: Sep. 13, 2013

(86) PCT No.: PCT/US2013/059688
§ 371 (c)(1),
(2) Date: Mar. 10, 2015

(87) PCT Pub. No.: WO2014/043490
PCT Pub. Date: Mar. 20, 2014

(65) Prior Publication Data
US 2015/0230460 A1     Aug. 20, 2015

Related U.S. Application Data

(60) Provisional application No. 61/701,881, filed on Sep. 17, 2012.

(51) Int. Cl.
*A01N 31/02* (2006.01)
*A61K 31/131* (2006.01)
*A61K 31/02* (2006.01)
*A01N 37/30* (2006.01)
*A01N 33/08* (2006.01)
*C02F 1/50* (2006.01)
*C02F 103/02* (2006.01)

(52) U.S. Cl.
CPC .............. *A01N 37/30* (2013.01); *A01N 33/08* (2013.01); *C02F 1/50* (2013.01); *C02F 2103/023* (2013.01); *C02F 2303/04* (2013.01)

(58) Field of Classification Search
CPC ....... A61K 31/02; A61K 31/131; A01N 31/02
USPC .......................................... 514/616, 628, 665
See application file for complete search history.

(56) References Cited

U.S. PATENT DOCUMENTS

| | | | |
|---|---|---|---|
| 4,800,082 A | 1/1989 | Karbowski et al. | |
| 4,816,061 A | 3/1989 | Walter, Jr. et al. | |
| 4,916,159 A * | 4/1990 | Whitekettle | A01N 37/34 162/161 |
| 2004/0261196 A1 | 12/2004 | Ghosh et al. | |
| 2010/0314318 A1 | 12/2010 | Gartner et al. | |
| 2012/0172430 A1 | 7/2012 | Yin et al. | |

* cited by examiner

*Primary Examiner* — Kamal Saeed
*Assistant Examiner* — Janet L Coppins
(74) *Attorney, Agent, or Firm* — Kenneth Crimaldi

(57) ABSTRACT

A synergistic microbicidal composition containing 2-(decylthio)ethanamine or its hydrochloride salt and 2,2-dibromomalonamide in a weight ratio from 64/1 to 1/16.

7 Claims, No Drawings

MICROBICIDAL COMPOSITION

This invention relates to a synergistic combination of selected microbicides having greater activity than would be observed for the individual microbicides.

In some cases, commercial microbicides cannot provide effective control of microorganisms, even at high use concentrations, due to weak activity against certain types of microorganisms, e.g., those resistant to some microbicides, or due to aggressive environmental conditions. Combinations of different microbicides are sometimes used to provide overall control of microorganisms in a particular end use environment. For example, U.S. Pat. App. Pub. No. 2004/0261196 discloses compositions containing DBMAL, but does not disclose any synergistic combinations. There is a need for combinations of microbicides having synergistic activity against various strains of microorganisms to provide effective control of the microorganisms. Moreover, there is a need for such combinations containing lower levels of individual microbicides for environmental and economic benefit. The problem addressed by this invention is to provide such synergistic combinations of microbicides.

STATEMENT OF THE INVENTION

The present invention is directed to a synergistic microbicidal composition comprising: (a) 2-(decylthio)ethanamine or its hydrochloride salt; and (b) 2,2-dibromomalonamide; wherein a weight ratio of (a)/(b) is from 64/1 to 1/16.

The present invention is further directed to methods for inhibiting growth of aerobic bacteria or anaerobic bacteria in an aqueous medium by adding 2-(decylthio)ethanamine or its hydrochloride salt and 2,2-dibromomalonamide to the aqueous medium.

DETAILED DESCRIPTION OF THE INVENTION

As used herein, the following terms have the designated definitions, unless the context clearly indicates otherwise. "DBMAL" is 2,2-dibromomalonamide (CAS no. 73003-80-2), also known as 2,2-dibromopropanediamide. "DTEA" is 2-(decylthio)ethanamine hydrochloride or 2-(decylthio)ethanamine; preferably DTEA is used in the form of its hydrochloride salt. The term "microbicide" refers to a compound capable of killing, inhibiting the growth of or controlling the growth of microorganisms at a locus; microbicides include bactericides, fungicides and algaecides. The term "microorganism" includes, for example, fungi (such as yeast and mold), bacteria and algae. The term "locus" refers to an industrial system or product subject to contamination by microorganisms. The following abbreviations are used throughout the specification: ppm=parts per million by weight (weight/weight), mL=milliliter, ATCC=American Type Culture Collection, MBC=minimum biocidal concentration, and MIC=minimum inhibitory concentration. Unless otherwise specified, temperatures are in degrees centigrade (° C.), and references to percentages are by weight (wt %). Amounts of organic microbicides are given on an active ingredient basis in ppm (w/w).

The compositions of the present invention unexpectedly have been found to provide enhanced microbicidal efficacy at a combined active ingredient level lower than that of the individual microbicides. Additional microbicides beyond those listed in the claims may be present in the composition. Preferably, the microbicidal composition is substantially free of microbicidal agents other than DBMAL and DTEA, i.e., it has less than 1 wt % of other microbicidal agents based on the weight of DBMAL and DTEA, preferably less than 0.5 wt %, preferably less than 0.2 wt %, preferably less than 0.1 wt %.

Preferably, 2-(decylthio)ethanamine or its hydrochloride salt and 2,2-dibromomalonamide are used to inhibit growth of anaerobic bacteria, preferably in a weight ratio of DTEA/DBMAL from 2/1 to 1/16, preferably from 2/1 to 1/10, preferably from 2/1 to 1/8. Preferably, the synergistic microbicidal composition is used to inhibit growth of *Desulfovibrio longus*, preferably in aqueous fluids used in oil or natural gas production. Preferably, DTEA and DBMAL are used to inhibit growth of aerobic bacteria, preferably to inhibit growth of *Pseudomonas aeruginosa*; preferably, a weight ratio of DTEA/DBMAL is from 64/1 to 1/8, preferably from 32/1 to 1/8. Preferably, the synergistic microbicidal composition is used to inhibit growth of aerobic bacteria, preferably in industrial water, preferably at a total active ingredient concentration from 5 ppm to 500 ppm, preferably 10 ppm to 250 ppm, preferably 10 ppm to 150 ppm.

The microbicides in the composition of this invention may be used "as is" or may first be formulated with a solvent or a solid carrier. Suitable solvents include, for example, water; glycols, such as ethylene glycol, propylene glycol, diethylene glycol, dipropylene glycol, polyethylene glycol, and polypropylene glycol; glycol ethers; alcohols, such as methanol, ethanol, propanol, phenethyl alcohol and phenoxypropanol; ketones, such as acetone and methyl ethyl ketone; esters, such as ethyl acetate, butyl acetate, triacetyl citrate, and glycerol triacetate; carbonates, such as propylene carbonate and dimethyl carbonate; and mixtures thereof. It is preferred that the solvent is selected from water, glycols, glycol ethers, esters and mixtures thereof. Suitable solid carriers include, for example, cyclodextrin, silicas, diatomaceous earth, waxes, cellulosic materials, alkali and alkaline earth (e.g., sodium, magnesium, potassium), montmorillonite, zeolite, layered double hydroxide metal salts (e.g., chloride, nitrate, bromide, sulfate) and charcoal.

A microbicide component can be formulated in the form of an emulsion, dispersion or solution. The solvent component can be an organic solvent or water, preferably water. Such mixtures can contain adjuvants, co-solvents, thickeners, antifreeze agents, emulsifiers, dispersants, fillers, pigments, surfactants, biodispersants, defoamers, sulfosuccinates, terpenes, furanones, polycations, stabilizers, scale inhibitors and anti-corrosion additives.

When both microbicides are each first formulated with a solvent, the solvent used for the first microbicide may be the same as or different from the solvent used to formulate the other commercial microbicide, although water is preferred for most industrial biocide applications. It is preferred that the two solvents are miscible.

Those skilled in the art will recognize that the microbicide components of the present invention may be added to a locus sequentially, simultaneously, or may be combined before being added to the locus. It is preferred that the first microbicide and the second microbicide component be added to a locus simultaneously or sequentially. When the microbicides are added simultaneously or sequentially, each individual component may contain adjuvants, solvent, thickeners, antifreeze agents, colorants, sequestrants (such as ethylenediaminetetraacetic acid, ethylenediaminedisuccinic acid, iminodisuccinic acid and salts thereof), dispersants, surfactants, biodispersants, sulfosuccinates, terpenes, furanones, polycations, stabilizers, scale inhibitors and anti-corrosion additives.

The microbicidal compositions of the present invention can be used to inhibit the growth of microorganisms or higher forms of aquatic life (such as protozoans, invertebrates, bryozoans, dinoflagellates, crustaceans, mollusks, etc.) by introducing a microbicidally effective amount of the compositions onto, into, or at a locus subject to microbial attack. Suitable loci include, for example: industrial process water; electrocoat deposition systems; cooling towers; air washers; gas scrubbers; mineral slurries; wastewater treatment; ornamental fountains; reverse osmosis filtration; ultrafiltration; ballast water; evaporative condensers; heat exchangers; pulp and paper processing fluids and additives; starch; plastics; emulsions; dispersions; paints; latices; coatings, such as varnishes; construction products, such as mastics, caulks, and sealants; construction adhesives, such as ceramic adhesives, carpet backing adhesives, and laminating adhesives; industrial or consumer adhesives; photographic chemicals; printing fluids, colorants; household products, such as bathroom and kitchen cleaners and sanitary wipes; cosmetics; toiletries; shampoos; soaps; detergents; industrial cleaners; floor polishes; laundry rinse water; metalworking fluids; conveyor lubricants; hydraulic fluids; leather and leather products; textiles; textile products; wood and wood products, such as plywood, chipboard, wallboard, flakeboard, laminated beams, oriented strandboard, hardboard, and particleboard; petroleum processing fluids; fuel; oilfield fluids, such as injection water, fracture fluids, and drilling muds; agriculture adjuvant preservation; preservation of agricultural products, surfactant preservation; medical devices; diagnostic reagent preservation; food preservation, such as plastic or paper food wrap; food, beverage, and industrial process pasteurizers; toilet bowls; recreational water; pools; and spas.

Preferably, the microbicidal compositions of the present invention are used to inhibit the growth of microorganisms at a locus selected from one or more of industrial process water; cooling towers; air washers; gas scrubbers; oilfield fluids, such as injection water, fracture fluids, and drilling muds; mineral slurries; wastewater treatment; mineral slurries, pulp and paper processing fluids and additives, starch, emulsions, dispersions, paints, latices, coatings, construction adhesives, such as ceramic adhesives, carpet backing adhesives, photographic chemicals, printing fluids, colorants, household products such as bathroom and kitchen cleaners and sanitary wipes, cosmetics, toiletries, shampoos, soaps, detergents, industrial cleaners, floor polishes, laundry rinse water, metal working fluids, textile products, wood and wood products, preservation of agricultural products and agricultural adjuvants, surfactant preservation, diagnostic reagent preservation, food preservation, and food, beverage, and industrial process pasteurizers.

The specific amount of the composition of this invention necessary to inhibit or control the growth of microorganisms and higher aquatic life forms in a locus depends upon the particular locus to be protected. Typically, the amount of the composition of the present invention to control the growth of microorganisms in a locus is sufficient if it provides from 1 to 500 ppm of the active ingredient of the composition in the locus. It is preferred that the active ingredients of the composition be present in the locus in an amount of at least 5 ppm, preferably at least 10 ppm, preferably at least 15 ppm. It is preferred that the active ingredients of the composition be present in the locus in an amount of no more than 500 ppm, preferably no more than 250 ppm, preferably no more than 150 ppm, preferably no more than 100 ppm.

EXAMPLES

The synergism of the biocides combination of the present invention was determined using the method described by Kull, F. C, et. al. in *Applied Microbiology* 9:538-541 (1961).

The formula to calculate the synergistic index (SI) is $$Qa/QA+Qb/QB=SI$$

where

QA=concentration of compound A in ppm, acting alone produced an end point or if end point could not be established, the highest concentration tested will be used as the end point for the calculation and the SI will be recorded in "less than or <" values Qa=concentration of compound A in ppm, in the mixture, which produced an end point QB=concentration of compound B in ppm, acting alone produced an end point or if end point could not be established, the highest concentration tested will be used as the end point for the calculation and the SI will be recorded in "less than or <" values Qb=concentration of compound B in ppm, in the mixture, which produced an end point Synergism within two biocides is demonstrated when the SI has a value less than 1. The mixtures showed an additive effect if SI is equal to 1 and antagonistic if SI is greater than 1.

Example 1

Biocidal Efficacy of DBMAL, DTEA, and their Combinations against Anaerobic Bacteria Inside an anaerobic chamber (BACTRON anaerobic chamber), a deoxygenated sterile salt solution (3.1183 g of NaCl, 1.3082 mg of $NaHCO_3$, 47.70 mg of KCl, 72.00 mg of $CaCl_2$, 54.49 mg of $MgSO_4$, 172.28 mg of $Na_2SO_4$, 43.92 mg of $Na_2CO_3$ in 1 L water) was inoculated with *Desulfovibrio longus* ATCC 51456, a sulfate-reducing bacterium, to a final bacterial concentration of $10^7$ to $10^8$ CFU/mL. Aliquots of this cell suspension were then treated with DBMAL, DTEA (in the hydrochloride form), and DBMAL/DTEA blends, at selected active concentrations. After the treated cell suspensions were incubated at 35° C. for 2 hours, the biocidal efficacy was determined by minimum tested biocide concentration for 99.999% bacteria kill in the aliquots. Table 1 summarizes the efficacy of each biocide and their blends, and the Synergy Index (SI) of each combination.

TABLE 1

Biocidal efficacy of DBMAL, DTEA, and DBMAL/DTEA blends against *Desulfovibrio longus* and resulting Synergy Index* values

| Active weight ratio of | Concentration (ppm a.i.) for more than 99.999% bacterial kill in 2 hours | | Synergy |
|---|---|---|---|
| DTEA:DBMAL | DTEA | DBMAL | Index |
| DTEA alone | 25.00 | 0.00 | |
| 2:1 | 12.50 | 6.25 | 0.56 |
| 1:1 | 12.50 | 12.50 | 0.63 |
| 1:4 | 6.25 | 25.00 | 0.50 |
| 1:8 | 6.25 | 50.00 | 0.75 |
| 1:16 | 3.13 | 50.00 | 0.63 |
| DBMAL alone | 0.00 | 100.00 | |

Example 2

Efficacy of DBMAL, DTEA, and their Combinations against Aerobic Bacteria

Synthetic cooling water was generated as disclosed in Appendix A and dispensed into three 96-well plates. A stock solution of DBMAL from 12% liquid active (or DBNPA from a solid formulation as appropriate) and a stock solution of DTEA (in the hydrochloride form) derived from a liquid stock stored under anaerobic conditions were generated in the synthetic cooling water. In one 96-well biocide block, the stock solution of DBMAL (or DBNPA as listed) was added to the first row of the master block and diluted 1:1 by row until the testing range has been prepared. In a second 96-well biocide block, the stock solution of DTEA was added to the first column of the master block and diluted 1:1 by column until the testing range has been prepared. Biocides from each DBMAL row in the DBMAL biocide master block were added to the matching experimental row in a 3rd 96 well plate filled with synthetic cooling water. This was repeated, adding biocides from each DTEA column from the DTEA biocide master block to the matching experimental column Working quickly, the following organisms were added from a cell-suspension with an OD600 of ~0.4 (approximately $1\times10^8$ cfu/ml) to final concentration of $1\times10^7$ cfu/ml in the first of the 96 well plates: *Pseudomonas aeruginosa* ATCC 10145, *Aeromonas hydrophila* ATCC 7965, and *Myroides odoratus* (*Flavobacterium odoratum*) NCIMB 13294. The resulting bacterial final concentration was $3\times10^7$ cfu/ml in the experimental 96 well block.

The experimental block was placed at 35° C., with the time of exposure started once the last well had been inoculated. At 4 hours, the experimental block was removed from the incubator, and 20 μl of treated cells from each row of the experimental block and were added to the first row of a 96-well plate pre-filled with TSB/Resazurin dye. Each sample from the first row of the TSB/Resazurin dye plate was diluted 1:10 six times by serial dilution moving down the plate by row. The inoculated TSB/Resazurin dye 96-well plate was placed at 35° C. for 24 hours, following that time data interpretation occurred. Color change from purple to pink indicates microbial metabolic activity and designates lack of cell death. Those wells were counted as "growth". Failure to have color change from purple to pink indicates a lack of microbial metabolic activity and designates cell death. These were counted as "no growth". Synergy was determined at the point where the control wells failed to kill cells but each tested biocide provided cell death at the same or lower dosage when used in combination. All combinations that showed synergy effect in 4 separate experiments were summarized in Table 2 to 5. The efficacy and synergy index of each combo were also included.

TABLE 2

DBMAL and DTEA combinations that are synergistic against aerobic bacteria—experiment 1

| Active weight ratio of DTEA:DBMAL | Concentration (ppm a.i.) for complete bacterial kill in 4 hours | | Synergy Index |
|---|---|---|---|
| | DTEA | DBMAL | |
| DTEA alone | 12.50 | 0.00 | |
| 2:1 | 12.50 | 6.25 | 1.25 |
| 1:1 | 6.25 | 6.25 | 0.75 |
| 4:1 | 12.50 | 3.12 | 1.12 |
| DBMAL alone | 0.00 | 25.00 | |

TABLE 3

DBMAL and DTEA combinations that are synergistic against aerobic bacteria—experiment 2

| Active weight ratio of DTEA:DBMAL | Concentration (ppm a.i.) for complete bacterial kill in 4 hours | | Synergy Index |
|---|---|---|---|
| | DTEA | DBMAL | |
| DTEA alone | 25.00 | 0.00 | |
| 2:1 | 12.50 | 6.25 | 0.75 |
| 1:1 | 6.25 | 6.25 | 0.50 |
| 4:1 | 12.50 | 3.12 | 0.62 |
| DBMAL alone | 0.00 | 25.00 | |

TABLE 4

DBMAL and DTEA combinations that are synergistic against aerobic bacteria—experiment 3

| Active weight ratio of DTEA:DBMAL | Concentration (ppm a.i.) for complete bacterial kill in 4 hours | | Synergy Index |
|---|---|---|---|
| | DTEA | DBMAL | |
| DTEA alone | 25.00 | 0.00 | |
| 4:1 | 12.50 | 3.13 | 0.63 |
| 2:1 | 12.50 | 6.25 | 0.75 |
| 1:1 | 6.25 | 6.25 | 0.50 |
| 1:2 | 3.13 | 6.25 | 0.38 |
| 1:4 | 3.13 | 12.50 | 0.63 |
| DBMAL alone | 0.00 | 25.00 | 1.00 |

TABLE 5

DBMAL and DTEA combinations that are synergistic against aerobic bacteria—experiment 4

| Active weight ratio of DTEA:DBMAL | Concentration (ppm a.i.) for complete bacterial kill in 4 hours | | Synergy Index |
|---|---|---|---|
| | DTEA | DBMAL | |
| DTEA alone | 100.00 | 0.00 | |
| 64:1 | 50.00 | 0.78 | 0.52 |
| 32:1 | 50.00 | 1.56 | 0.53 |
| 16:1 | 50.00 | 3.13 | 0.56 |
| 8:1 | 50.00 | 6.25 | 0.63 |
| 4:1 | 25.00 | 6.25 | 0.38 |
| 2:1 | 25.00 | 12.50 | 0.50 |
| 1:1 | 12.50 | 12.50 | 0.38 |
| 1:2 | 6.25 | 12.50 | 0.31 |
| 1:4 | 6.25 | 25.00 | 0.56 |
| 1:8 | 3.13 | 25.00 | 0.53 |
| DBMAL alone | 0.00 | 50.00 | |

In order to differentiate DBMAL/DTEA combinations from DTEA/DBNPA combinations, DTEA/DBNPA combinations were also tested using the same test procedures and conditions described above. Biocidal efficacy of DBNPA/DTEA combinations against anaerobic bacteria was summarized in Table 6. All combinations that showed synergy effect against aerobic bacteria in 3 separate experiments were summarized in Table 7 to 9.

TABLE 6

Biocidal efficacy of DBNPA, DTEA, and DBNPA/DTEA blends against *Desulfovibrio longus* and resulting Synergy Index values

| Active weight ratio of | Concentration (ppm a.i.) for more than 99.999% bacterial kill in 2 hours | | Synergy Index |
|---|---|---|---|
| DTEA:DBNPA | DTEA | DBNPA | |
| DTEA alone | 25.00 | 0.00 | |
| 2:1 | 12.50 | 6.25 | 0.75 |
| 1:1 | 12.50 | 12.50 | 1.00 |
| 1:4 | 6.25 | 25.00 | 1.25 |
| 1:8 | 3.13 | 25.00 | 1.13 |
| 1:16 | 1.63 | 25.00 | 1.07 |
| DBNPA alone | 0.00 | 25.00 | |

TABLE 7

DBNPA and DTEA combinations that are synergistic against aerobic bacteria—experiment 5

| Active weight ratio of | Concentration (ppm a.i.) for complete bacterial kill in 4 hours | | Synergy Index |
|---|---|---|---|
| DTEA:DBNPA | DTEA | DBNPA | |
| DTEA alone | 50.00 | 0.00 | |
| 32:1 | 25.00 | 0.78 | 0.62 |
| 16:1 | 25.00 | 1.56 | 0.75 |
| 8:1 | 12.50 | 1.56 | 0.50 |
| 4:1 | 12.50 | 3.13 | 0.75 |
| 2:1 | 6.25 | 3.13 | 0.63 |
| 1:1 | 3.13 | 3.13 | 0.56 |
| 1:2 | 1.56 | 3.13 | 0.53 |
| DBNPA alone | 0.00 | 6.25 | |

TABLE 8

DBNPA and DTEA combinations that are synergistic against aerobic bacteria—experiment 6

| Active weight ratio of | Concentration (ppm a.i.) for complete bacterial kill in 4 hours | | Synergy Index |
|---|---|---|---|
| DTEA:DBNPA | DTEA | DBNPA | |
| DTEA alone | 100.00 | 0.00 | |
| 32:1 | 50.00 | 1.56 | 0.75 |
| 16:1 | 25.00 | 1.56 | 0.50 |
| 8:1 | 25.00 | 3.13 | 0.75 |
| 4:1 | 12.50 | 3.13 | 0.63 |
| 2:1 | 6.25 | 3.13 | 0.56 |
| DBNPA alone | 0.00 | 6.25 | |

TABLE 9

DBNPA and DTEA combinations that are synergistic against aerobic bacteria—experiment 7

| Active weight ratio of | Concentration (ppm a.i.) for complete bacterial kill in 4 hours | | Synergy Index |
|---|---|---|---|
| DTEA:DBNPA | DTEA | DBNPA | |
| DTEA alone | 50.00 | 0.00 | |
| 16:1 | 25.00 | 1.56 | 0.75 |
| 8:1 | 12.50 | 1.56 | 0.50 |
| 4:1 | 12.50 | 3.13 | 0.25 |
| 2:1 | 6.25 | 3.13 | 0.63 |
| 1:1 | 3.13 | 3.13 | 0.56 |
| 1:2 | 1.56 | 3.13 | 0.53 |
| DBNPA alone | 0.00 | 6.25 | |

Results from Tables 6 to 9 demonstrate that DTEA/DBNPA combinations and DTEA/DBMAL combinations behaved differently when tested against both anaerobic and aerobic bacteria. Their synergistic blend ratios are different from each other.

APPENDIX A

Synthetic Cooling Tower Recipe
Stock Solutions A to E

Solution A:

| Salt/Chemical | g/250 mL DI water |
|---|---|
| $CaCl_2$ (anhydrous) | 11.08 |
| $MgCl_2 \cdot 6H_2O$ | 10.15 |

Solution B:

| Salt/Chemical | g/250 mL DI water |
|---|---|
| $Na_2CO_3$ (anhydrous) | 5.27 |

Solution C:

| Salt/Chemical | g/250 mL DI water |
|---|---|
| Glucose (anhydrous) | 0.003 |
| $NH_4NO_3$ | 1.43 |
| $K_2HPO_4$ (anhydrous) | 0.57 |
| Yeast Extract | 0.0003 |

Solution D:

| Salt/Chemical | g/250 mL DI water |
|---|---|
| $CuCl_2 \cdot 2H_2O$ | 0.017 |
| $FeCl_3$ (anhydrous) | 0.047 |

Solution E:

| Salt/Chemical | g/250 mL DI water |
|---|---|
| $K_2SO_4$ | 7.25 |

The stock solutions were filtered and sterilized and kept in a cool dark place.

The invention claimed is:

1. A synergistic microbicidal composition comprising: (a) 2-(decylthio)ethanamine or its hydrochloride salt; and (b) 2,2-dibromomalonamide; wherein a weight ratio of (a)/(b) is from 64/1 to 1/16.

2. A method for inhibiting growth of aerobic bacteria in an aqueous medium by adding 2-(decylthio)ethanamine or its hydrochloride salt and 2,2-dibromomalonamide to the aqueous medium.

3. The method of claim 2 in which a weight ratio of 2-(decylthio)ethanamine or its hydrochloride salt/2,2-dibromomalonamide is from 64/1 to 1/16.

4. The method of claim 3 in which the aqueous medium is industrial water.

5. A method for inhibiting growth of anaerobic bacteria in an aqueous medium by adding 2-(decylthio)ethanamine or its hydrochloride salt and 2,2-dibromomalonamide to the aqueous medium.

6. The method of claim 5 in which a weight ratio of 2-(decylthio)ethanamine or its hydrochloride salt/2,2-dibromomalonamide is from 2/1 to 1/16.

7. The method of claim 6 in which the aqueous medium is industrial water.

* * * * *